(12) United States Patent
Sexton

(10) Patent No.: US 11,712,523 B2
(45) Date of Patent: Aug. 1, 2023

(54) SECURE DEVICE FOR DELIVERING MEDICATIONS

(71) Applicant: Achilleus LLC, Kansas City, MO (US)

(72) Inventor: Brian Sexton, Chicago, IL (US)

(73) Assignee: ACHILLEUS LLC, Kansas City, MO (US)

( * ) Notice: Subject to any disclaimer, the term of this patent is extended or adjusted under 35 U.S.C. 154(b) by 660 days.

(21) Appl. No.: 16/588,947

(22) Filed: Sep. 30, 2019

(65) Prior Publication Data

US 2020/0101232 A1    Apr. 2, 2020

Related U.S. Application Data

(60) Provisional application No. 62/738,699, filed on Sep. 28, 2018.

(51) Int. Cl.
*A61M 5/31* (2006.01)
*A61M 5/315* (2006.01)
*A61M 5/20* (2006.01)

(52) U.S. Cl.
CPC .... *A61M 5/31571* (2013.01); *A61M 5/31573* (2013.01); *A61M 2005/2073* (2013.01); *A61M 2205/276* (2013.01); *A61M 2205/3584* (2013.01); *A61M 2205/60* (2013.01); *A61M 2210/0618* (2013.01)

(58) Field of Classification Search
CPC .......... A61M 5/31571; A61M 5/31573; A61M 2005/2073; A61M 5/31501
See application file for complete search history.

(56) References Cited

U.S. PATENT DOCUMENTS 4,657,490 A * 4/1987 Abbott .............. A61M 5/14224
417/478
5,429,600 A * 7/1995 Heinke .................... A61D 7/00
604/87

(Continued)

FOREIGN PATENT DOCUMENTS

GB         2534469 A  *  7/2016  ............ A61M 5/315
WO     2015038092 A2     3/2015

OTHER PUBLICATIONS

International Search Report and Written Opinion of PCT/US2019/053906 dated Dec. 4, 2019.

*Primary Examiner* — Courtney B Fredrickson
(74) *Attorney, Agent, or Firm* — Husch Blackwell LLP

(57) ABSTRACT

A method and device for delivering medications that includes a syringe body, a cartridge nest with an application tip, a plunger actuator, and an electronic lock subassembly adapted for preventing administration of the medication until specific conditions are met. The medicine cartridge may comprise a form of a digital security key to prevent the device from administering medication unless specific configurations and conditions are met. The device may further be adapted with pre-programmed information and may be used with a smartphone, tablet, or computer application. The electronic lock subassembly will only permit the administration of medicine when the patient and/or administrator is verified via facial and voice recognition, biometric identifier, or other unique information. Upon proper permission, the device may be used to administer medicine, including injecting medicine into the nasal cavity of a patient.

19 Claims, 13 Drawing Sheets

(56) References Cited

U.S. PATENT DOCUMENTS

| | | |
|---|---|---|
| 8,231,588 B2 | 7/2012 | Xia |
| 8,690,839 B2 | 4/2014 | Xia et al. |
| 8,876,794 B2 | 11/2014 | Xia |
| 8,905,980 B2 | 12/2014 | Xia |
| 9,597,486 B2 | 3/2017 | Xia |
| 2004/0082918 A1 | 4/2004 | Evans et al. |
| 2004/0236283 A1* | 11/2004 | Tang ............... A61M 5/322 604/110 |
| 2006/0021614 A1 | 2/2006 | Wermeling et al. |
| 2011/0098658 A1* | 4/2011 | Enggaard ........... A61M 5/3155 604/207 |
| 2011/0270214 A1 | 11/2011 | Jorgenson et al. |
| 2012/0323208 A1* | 12/2012 | Bochenko ............ A61J 1/2096 604/404 |
| 2013/0131586 A1 | 5/2013 | Poutiatine et al. |
| 2015/0144793 A1* | 5/2015 | Whalley ............... G01F 13/00 250/357.1 |
| 2016/0012205 A1* | 1/2016 | Saint ............... A61M 5/31528 604/189 |
| 2017/0197025 A1* | 7/2017 | Adams ................. G16Z 99/00 |
| 2017/0232300 A1* | 8/2017 | Tran ..................... A63B 71/06 434/247 |
| 2019/0054247 A1* | 2/2019 | Dantsker ........... A61M 5/31553 |

\* cited by examiner

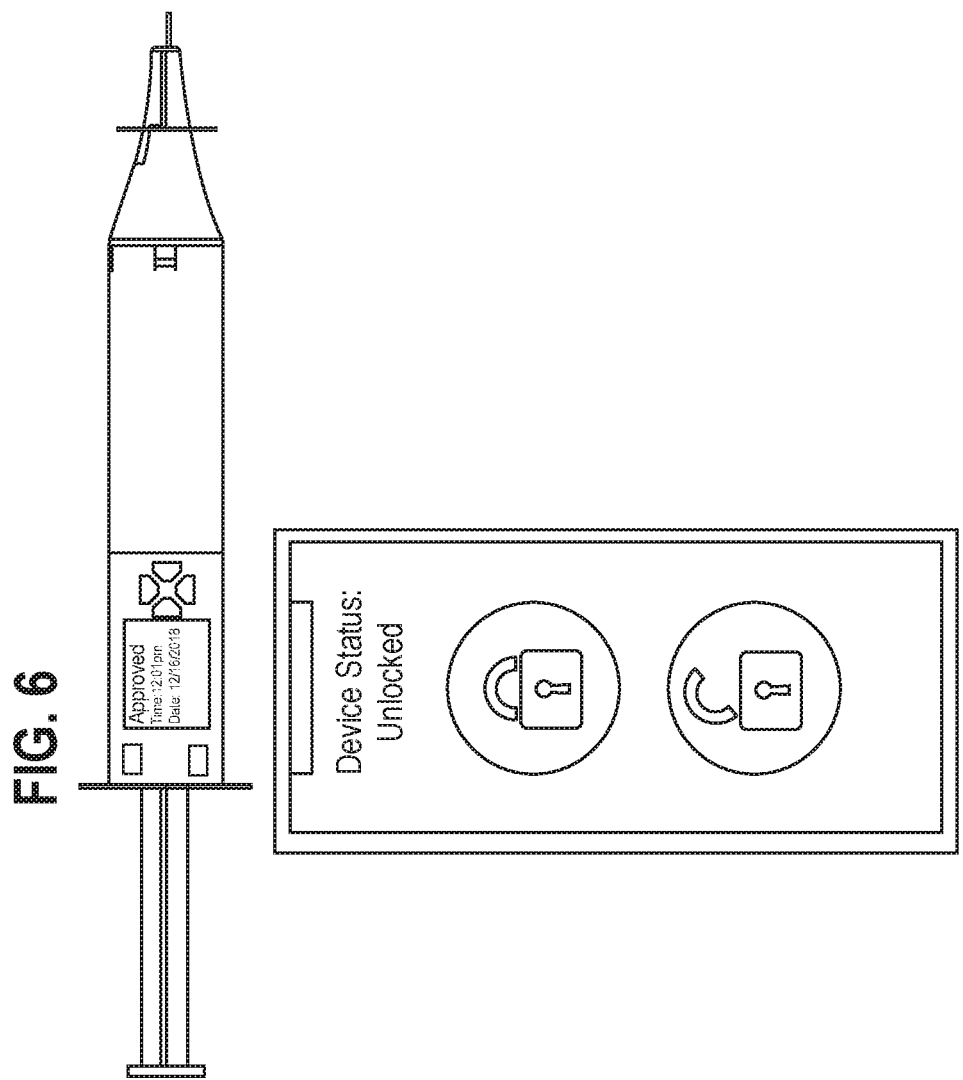

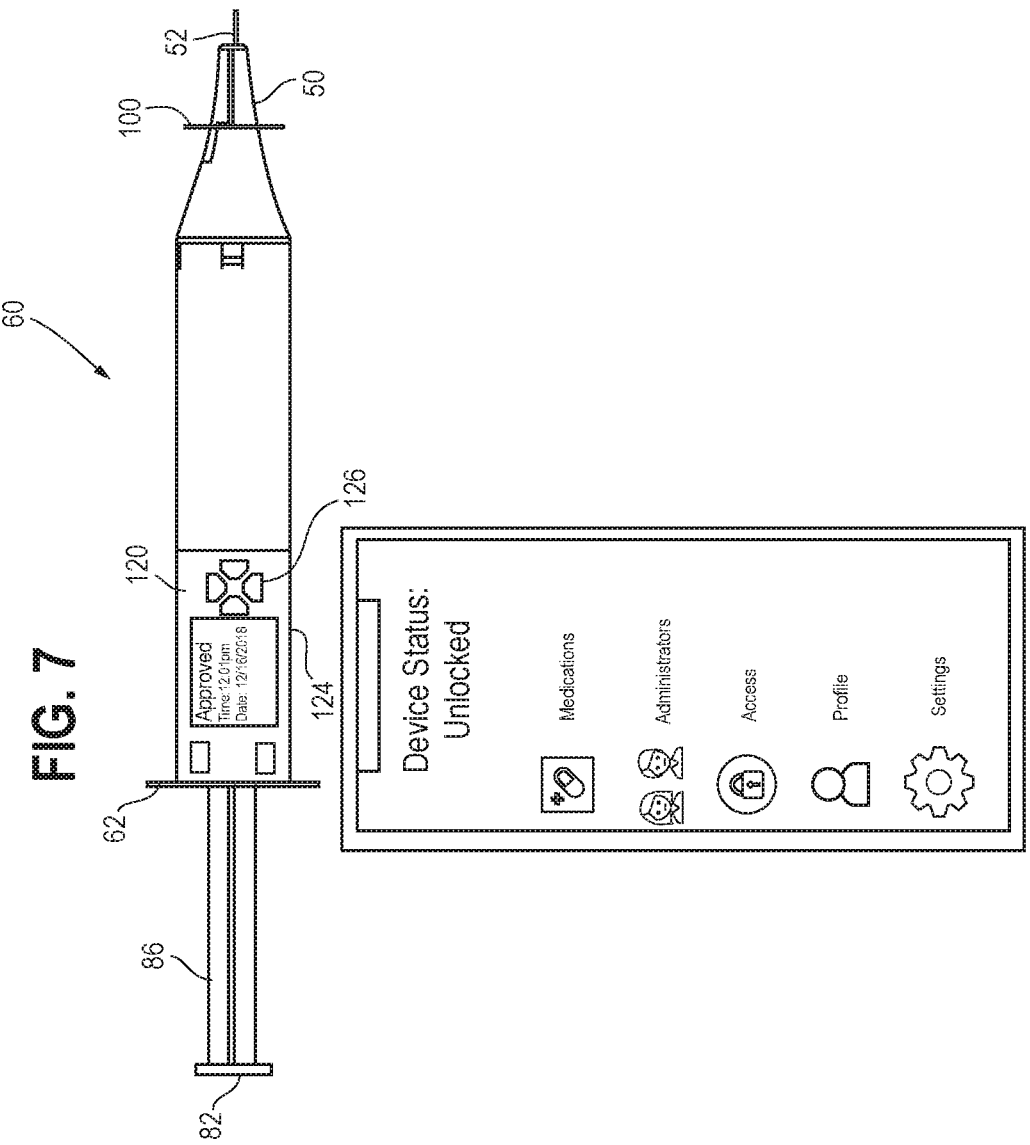

SECURE DEVICE FOR DELIVERING MEDICATIONS

CROSS-REFERENCE TO RELATED APPLICATIONS

This Application claims priority to U.S. Provisional Patent Application Ser. No. 62/738,699, filed on Sep. 28, 2018, to Brian Sexton, entitled "Secure Device for Delivering Intranasal Medication," the entire disclosure of which is incorporated herein by reference.

FIELD OF THE INVENTION

The present invention is generally directed to systems and methods for delivering medications, including intranasal medications, while avoiding abuse and misuse.

BACKGROUND

Intranasal medications may be delivered by way of an injector through a nasal passage of a patient and into a region medial, posterior, and/or inferior to a sphenopalatine ganglion of the patient. Currently known devices generally provide comfort and convenience for the patient and the applicator, and are often used for administering pain medications. Currently known generally unsecure devices risk being abused and misused. Existing devices are contributing to an ongoing opioid epidemic in the United States and elsewhere. Accordingly, there is a need for a device that can prevent misuse and abuse of pain medications, while allowing accurate and convenient control for medical professionals.

SUMMARY OF THE INVENTION

The secure device or syringe of the present invention may be adapted for requiring a form of verification between the syringe actuator and the medication. Individual medications can be contained within a secured cartridge. The cartridge can be outfitted with an electronic unique identifier. In one embodiment, this cartridge may remain locked unless it is paired with a pre-approved syringe body. The identification of the medicine will contain information such as: approved administrator(s) (e.g., doctor, nurse, patient, etc.); medicine type, dose, and pre-approved syringe identification.

The cartridge can be loaded into a single-use, disposable, cartridge nest. The cartridge nest may be integrated with a soft, flexible, application tip that navigates through a patient's nasal cavity to reach the desired location within the sinuses.

The cartridge nest is loaded into the syringe body. The syringe body can contain additional security electronics. The security features contain authentication information. The information may contain, for example: pre-approved syringe identification, approved administrators, time stamp of application, location of application, approved medicines, approved doses, and Blockchain methodology for auditing.

Other and further objects of the invention, together with the features of novelty appurtenant thereto, will appear in the course of the following description.

BRIEF DESCRIPTION OF THE SEVERAL VIEWS OF THE DRAWING

In the accompanying drawings, which form a part of the specification and are to be read in conjunction therewith in which like reference numerals are used to indicate like or similar parts in the various views:

FIG. 6 is an example of a user interface for a mobile device along with a secure syringe in accordance with one embodiment of the present invention;

FIG. 7 is an example of a user interface for a mobile device along with a secure syringe in accordance with one embodiment of the present invention;

DESCRIPTION OF THE INVENTION

Figure 1:
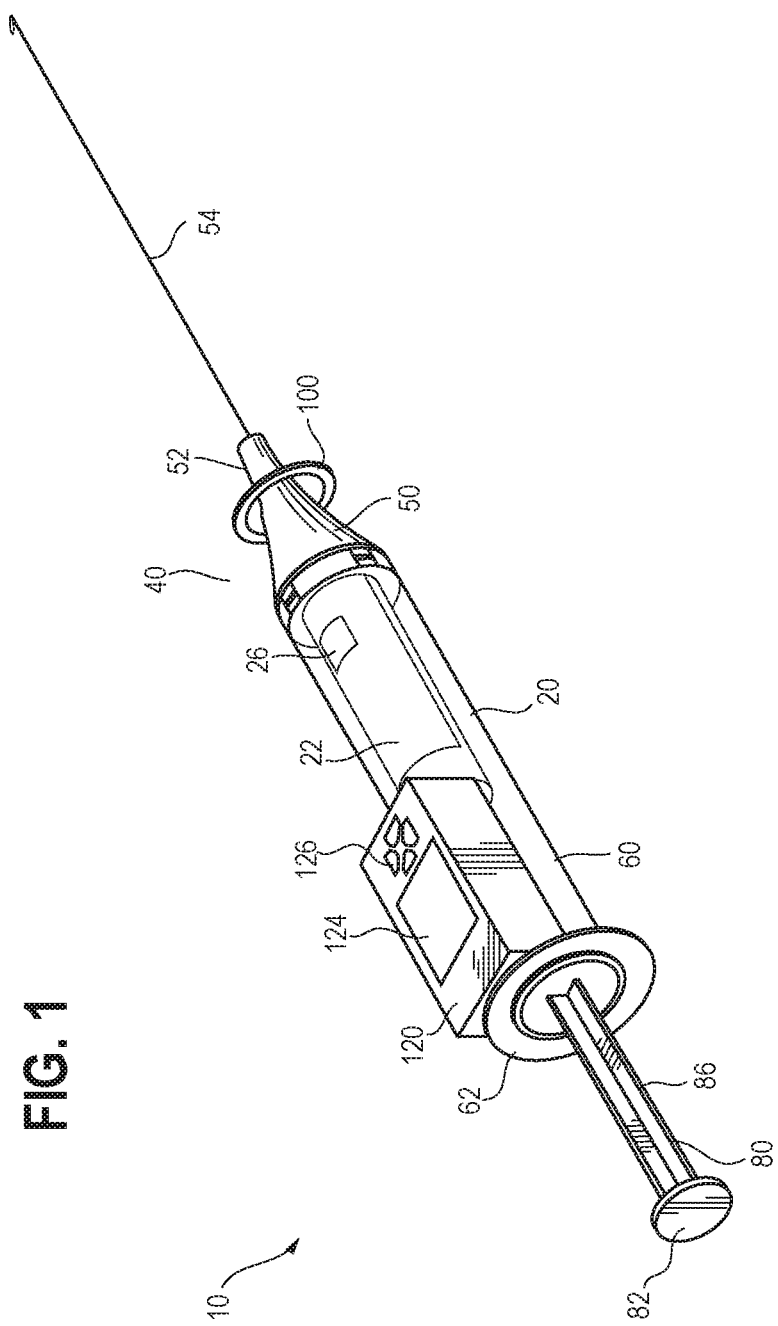
FIG. 1 is a perspective view of a secure syringe in accordance with one embodiment of the present invention.

The invention will now be described with reference to the drawing figures, in which like reference numerals refer to like parts throughout. For purposes of clarity in illustrating the characteristics of the present invention, proportional relationships of the elements have not necessarily been maintained in the drawing figures. It will be appreciated that any dimensions included in the drawing figures are simply provided as examples and dimensions other than those provided therein are also within the scope of the invention.

The following detailed description of the invention references specific embodiments in which the invention can be practiced. The embodiments are intended to describe aspects of the invention in sufficient detail to enable those skilled in the art to practice the invention. Other embodiments can be utilized, and changes can be made without departing from the scope of the present invention. The present invention is defined by the appended claims and the description is, therefore, not to be taken in a limiting sense and shall not limit the scope of equivalents to which such claims are entitled.

The present invention generally relates to a secure device 10 for delivering medications, such as intranasal medications. In one embodiment of the present invention, as demonstrated in FIGS. 1-5, the device 10 is comprised of a medicine cartridge 20 with integrated electronics, a cartridge nest with a flexible application tip 50, a syringe body 60 with integrated electronics, a plunger actuator 80, a nose guard 100, and an electronic and lock subassembly 120. It will be appreciated that in one preferred embodiment of the present invention the primary subject will be a human patient, but the present invention may also be used with other animals and a variety of other subjects. Additionally, it will be appreciated that in one preferred embodiment of the present invention, the device 10 will be used to inject medication into the nasal cavity the patient, but the present invention may also be used to inject other materials in other areas and via other means.

FIG. 1 illustrates one embodiment of a secure device 10 for administering and delivering medication to a patient. As shown, the device 10 may be in the form of a syringe, applicator device, or the like, although other types of devices are also within the scope of the present invention. As illustrated in the FIG. 1, the device 10 can include various sub-assemblies and components, such as a medicine cartridge 20, a cartridge nest with flexible application tip 50, a syringe body 60 with integrated electronics, a plunger actuator 80, a nose guard 100, and an electronics and lock subassembly 120.

Figure 2:
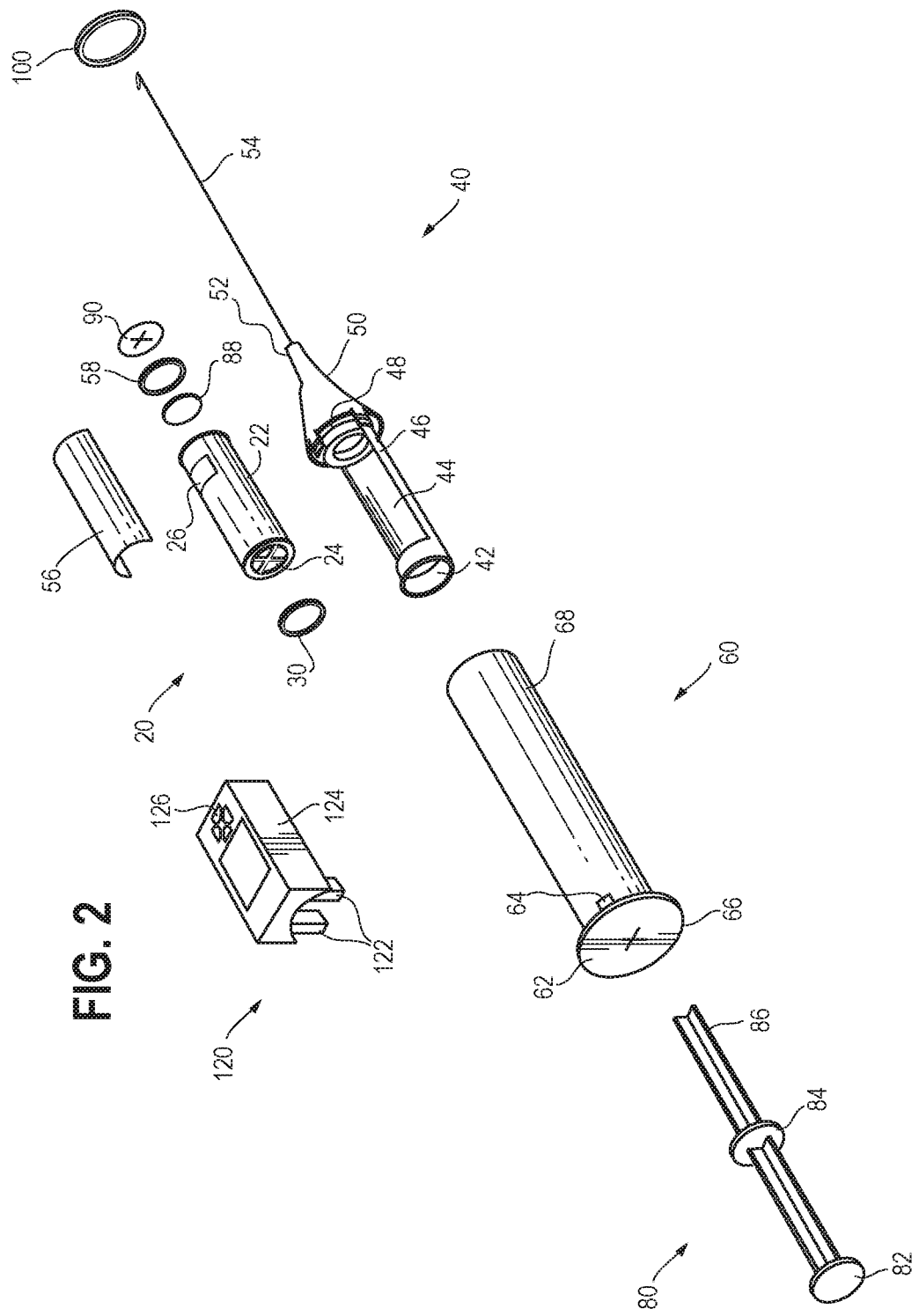
FIG. 2 is an exploded perspective view of a secure syringe in accordance with one embodiment of the present invention.

As illustrated in FIG. 2, in one embodiment of the present invention, the device 10 may comprise a medicine cartridge 20. The medicine cartridge 20 may comprise a top face seal 30, a bottom face seal 58, a medicine cartridge housing body 22, a medicine cartridge pattern 24, a radio frequency identification chip 26, and a dispensable barrier, which may be in the preferred embodiment a perforated film seal 90.

In one embodiment of the present invention, the device 10 may further comprise a cartridge nest 40 with a flexible application tip 50, as illustrated in FIGS. 1-2. The cartridge nest 40 may be made of a plastic, rubber, or other suitable material and the flexible application tip 50 may be formed of a soft rubber, plastic or other suitable flexible material. The flexible application tip 50 may be adapted for providing a comfortable method for applying medicine to the patient via a nasal cavity. The cartridge nest 40 may further be adapted for storage of the medicine cartridge 20. The cartridge nest 40 may be of a cylindrical, triangular, rectangular, or other polygonal shape, such that the medicine cartridge 20 may fit securely within the cartridge nest 40, and in the preferred embodiment, the medicine cartridge 20 may rest on the interior wall of the cartridge nest, specifically the cartridge nest body 44. The medicine cartridge 20 may be placed and/or removed from the cartridge nest by the removal of a cartridge nest cover 56. In one embodiment of device 10, the medicine cartridge 20 may be placed in the cartridge nest 40 before the syringe body 60 is attached to the cartridge nest 40.

The cartridge nest cover 56 may be of a shape and design such that the medicine cartridge 20 can be freely removed or placed within the cartridge nest. The cartridge nest 40 may further comprise a cartridge nest channel 52, located at the proximal end of the device 10, that may be used for the flowing or distribution of medicine or liquid from the medicine cartridge 20, when acted upon by the plunger actuator. The cartridge nest 40 may further comprise at the farthest proximal end of the device 10, the integrated flexible application injector 54. In one embodiment of the device 10, the integrated flexible application injector may be designed to be inserted into the nasal cavity of the patient, such that medicine may be pushed through the integrated flexible application injector 54 and injected into the nasal cavity of the patient. The integrated flexible application injector 54 may be made of an appropriate length, for individual patients, such that it may be long enough to enter the nasal cavity of the patient. The integrated flexible application injector 54 may be made from a variety of different materials, and may be made of a plastic polymer, glass, rubber, or other suitable materials now known or hereafter developed. The cartridge nest 40 may further comprise at least one cartridge nest tab 48 located near the proximal end of the cartridge nest 40. The at least one cartridge nest tab 48 may be used for locking or otherwise attaching the cartridge nest 40 to the syringe body 60 of the device 10. In one embodiment of device 10, the syringe body 60 may slide over the cartridge nest 40 until it reaches the cartridge nest tab 48. The cartridge nest tab 48 may be designed in a way such that it creates a mechanical fastening, thereby securing the syringe body to the cartridge nest.

In one embodiment of the present invention, the device 10 may further comprise a syringe body 60, as illustrated in FIGS. 1-2. The syringe body 60 may be cylindrical, triangular, rectangular, or other polygonal shapes in design. The syringe body 60 may be adapted to comprise integrated electronics and locking subassembly mechanism 120 coupled thereto. The electronics and locking subassembly mechanism 120 may contain the active electronics for securing the device 10. In one embodiment of the device 10, the syringe body 60 and electronics and locking subassembly mechanism 120 is intended to be reused by patients and/or doctors. It will be appreciated that in other embodiments the syringe body 60 and electronics and locking subassembly mechanism 120 could also be a single use, or disposable product. The syringe body 60 may be adapted to retain the cartridge nest 40 in a fixed location. By retaining the cartridge nest 40 in a fixed location, the plunger actuator 80 may be aligned with the medicine cartridge 20 for injecting medicine into the patient. The syringe body 60 can function to provide mechanical alignment and volume for packaging the security electronics.

As best illustrated in FIGS. 1-2, the syringe body 60 contour can include a syringe handle 62 for an improved fit, comfort, and usability of the device 10, providing the user a counterforce to the plunger actuator 80. The design of the syringe handle 62 can vary based on the embodiment and may be designed as having a circular, triangular, rectangular, or other polygonal shape. In one embodiment of the device 10, the syringe body 60 may further comprise pass-through indentions, recessed areas, or channels. For example, the syringe body 60 may include at least one syringe body locking channel 64 that permits a retractable feature from the electronics subassembly 120 to pass there through in order to prevent the plunger actuator 80 from moving and, thus, preventing the plunger actuator 80 from providing the pressure to inject medicine into the patient. In one embodiment of the device 10, the syringe body 60 may further comprise a uniquely-shaped passage 66 designed so that it may only be compatible with an approved plunger actuator 80 and may have the same design shape as the plunger actuator 80.

In one embodiment of device 10, as illustrated in FIGS. 1-2, the specially-shaped passage 66 may be designed in the cross-sectional shape of the plunger actuator 80. A specific embodiment of device 10, comprises a specially-shaped passage 66 in a design such that only a plunger actuator 80 designed by an approved manufacturer will be compatible with the device 10. This specific example is not limiting of the device 10, and the specially-shaped passage 66 may be designed in other shapes and designs and may work with plunger actuators designed and/or manufactured by other companies. The syringe body 60 can be made of a high strength plastic, rubber, or other material, and in a preferred embodiment the syringe body is made out of a high strength plastic. The syringe body 60 may optionally be reusable and contain all the active electronics needed for the security and data collection systems.

The syringe body 60 may further comprise an integrated electronics subassembly system 120 that may be used to lock the device 10 and prevent misuse of the device 10. The electronics and lock subassembly system 120 may be attached to the syringe body 60 through a fastening method including an adhesive or it may be attached through a mechanical means. In exemplary embodiments, the electronics and lock sub assembly system may be built or manufactured or otherwise permanently affixed to the syringe body 60. The integrated electronics subassembly systems may be located at the distal end of the syringe body 60, away from the flexible tip 50. In one embodiment of the device 10, the integrated electronics subassembly system 120 may be located on the outer surface of the syringe body 60 and additionally may be located near the syringe handle 62.

Figure 3:
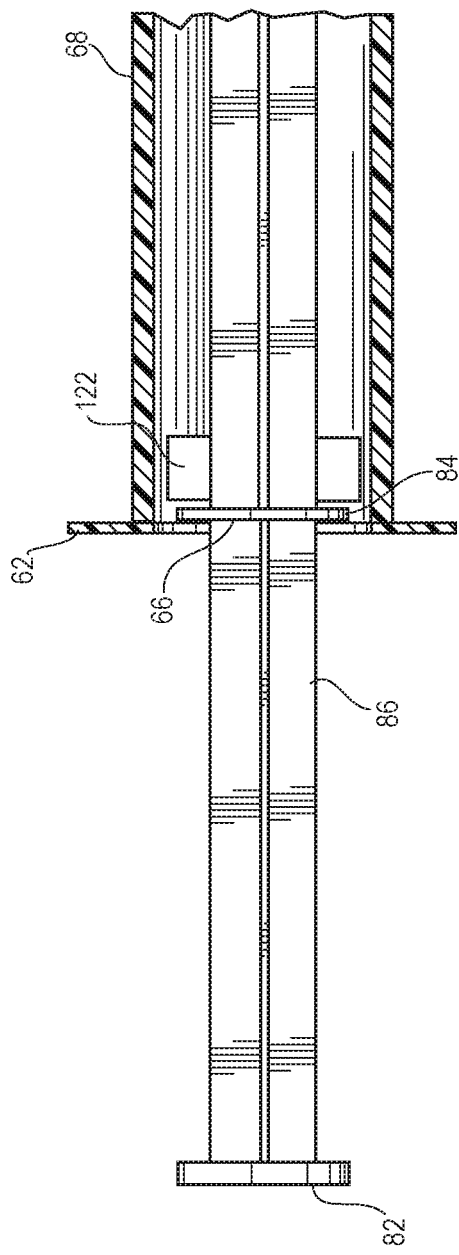
FIG. 3 is a partial side sectional view of a secure syringe illustrating a locking mechanism in accordance with one embodiment of the present invention.
Figure 5:
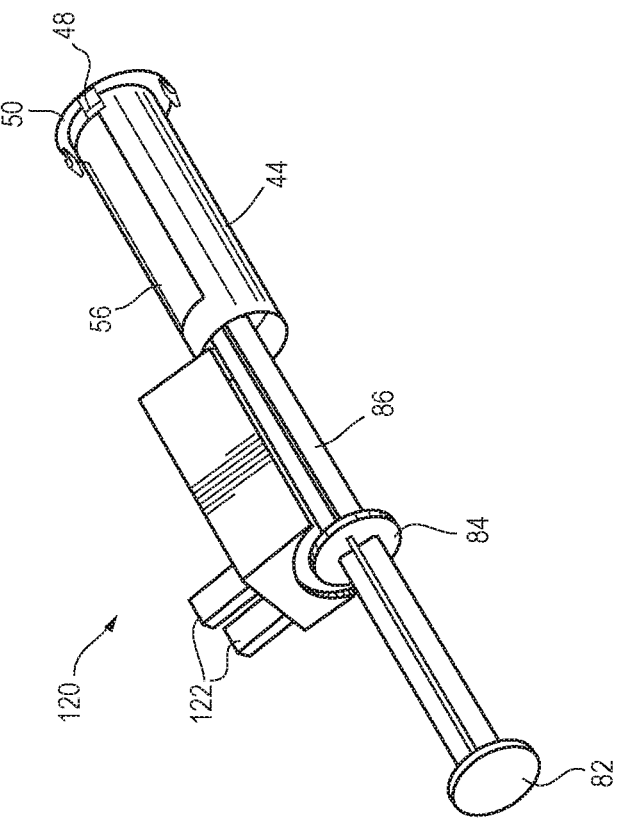
FIG. 5 is a partial perspective view sectional view of components of a secure syringe illustrating the locking mechanism in a disengaged or unlocked orientation in accordance with one embodiment of the present invention.
Figure 4:
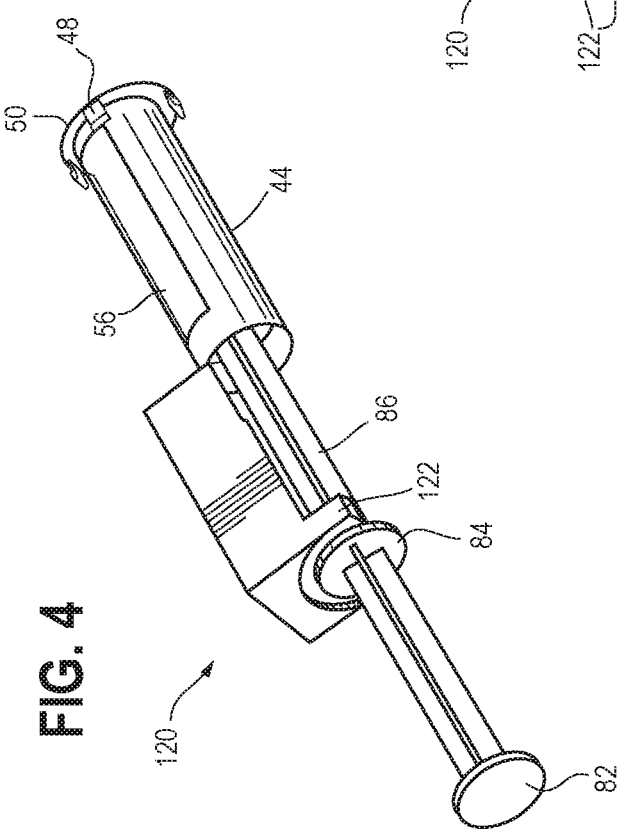
FIG. 4 is a partial perspective view of components of a secure syringe illustrating the locking mechanism in an engaged or locked orientation in accordance with one embodiment of the present invention.

The integrated electronics subassembly system 120 may comprise one or more high strength levers 122 for locking the device 10 and preventing the plunger actuator 80 from pushing through the device 10 and the medicine cartridge 20 and thereby preventing the injecting of medicine into the patient. To achieve this, the integrated electronics subassembly system 120 may selectively stroke or otherwise extend into the syringe body 60 and prevent the retaining surface on the plunger actuator 80 from moving axially and pressurizing the medicine cartridge 20. The high strength levers 122 may be retractable such that when medicine is to be administered in accordance with scheduling and security procedures, the high strength levers 122 may no longer retain the plunger actuator 80 so that medicine can be administered. In the illustrated embodiment, the high strength levers 122 may enter the syringe body 60 through the syringe body channel 64, and act as stopping point or block, preventing the plunger actuator 80 from pushing forward. When medicine needs to be administered, the high strength levers 122 may be retracted through the syringe body channel 64, allowing the plunger actuator 80 to extend through the syringe body 60 and medicine cartridge 20 to administer the medicine. The locking mechanism of the electronics and lock subassembly 120 is best illustrated in FIGS. 3-5. The electronics subassembly 120 may incorporate a display screen 124 to show status and menus and may be further used to control the locking mechanism and other functionalities of the device 10. The direction and selection buttons 126 allow the user to navigate through menus of the integrated electronics subassembly 120. The direction and selection buttons 126 may be comprised of directional buttons, such as up, down, and side-to-side buttons, or it may incorporate a wheel, touch screen, or other directional interfaces. In the embodiment illustrated in the figures, the directional selection button 126 comprise four buttons, corresponding to an up, down, left, and right selection.

In one embodiment, the device 10 may further comprise a plunger actuator 80 that can be uniquely keyed, coded, or otherwise uniquely identified, such that it is only compatible with a unique or particularized medicine cartridge 20 and syringe body 60. The plunger actuator 80 can be of a shape and/or design, such that it may be locked or otherwise prevented from pushing through the syringe body 60 and the medicine cartridge 20, allowing for a device that may be secured in order to prevent abuse. The design of one embodiment of the plunger actuator 80 is illustrated in FIGS. 1-5. The plunger actuator 80 may be disposable and may be disposed of after one, or more uses, or it may be reusable. The plunger actuator 80 may be retained by the syringe body 60. In another embodiment, the plunger actuator 80 may be removable from the syringe body 60 and may only be used when the device 10 is ready to be in use. It will be appreciated that the device 10 could utilize other methods of injection, and that the plunger actuator 80 is not intended to be a limiting design of the present invention.

The plunger actuator 80 may be formed of plastic, rubber, or other suitable materials and combination thereof. The plunger actuator 80 may comprise a finger engagement surface 82 at the distal end thereof. The plunger actuator 80 may further comprise a plunger tab 84, located at a point on the elongated plunger shaft 86 to help ensure the plunger actuator 80 stays retained within the syringe body 60. In a preferred embodiment of the present invention, the plunger actuator 80 features shaft 86 of a cross-sectional shape matching the cross-sectional shape of the specially-shaped channel 66 of the syringe body 60 and the medicine cartridge pattern 24. This particular cross-sectional shape may be of any suitable shape or design. One key feature of the design of the plunger actuator 80 is that it should match the design of the specially-shaped channel 66 of the syringe body 60 and the medicine cartridge pattern 24.

As illustrate in FIGS. 1-2, the device 10 may further comprise a nose guard 100. The nose guard 100 may be comprised of a nose guard ring 102 and a nose guard stem 104. The nose guard ring 100 may be designed to be generally circular in design, or it may be triangular, rectangular, or other polygonal shapes, such that the nose guard 100 may be used to prevent the flexible application tip 50 from penetrating too deeply into the nasal passage. The nose guard stem 104 may extend from the nose guard ring 102 towards the interior of the nose guard 100. The nose guard stem 104 may be used to secure the nose guard to the device 10. In one embodiment of the invention, the nose guard 100 may be connected to the flexible application tip 50, by inserting the nose guard stem 104 into the cartridge nest channel 52 and sliding the nose guard stem 104 through the cartridge nest channel 52 until the nose guard stem 104 locks in place, thereby securing the nose guard 100 to the device 10. The nose guard 100 may be a separate piece that can be affixed to the device 10, or it may be a separate piece assembled to the disposable cartridge nest 40 in order to prevent the contoured tip 50 of the cartridge nest 40 from inserting too deeply into the nasal cavity of the patient.

One embodiment of device 10 is illustrated in FIG. 2, which shows an exploded view of the device 10 in its general alignment and configuration. When fully assembled, the top face seal 30 may provide a backup seal between the cartridge nest 40 and the front, input side of the cartridge nest 40. The top face seal 30 may also provide a pre-load to the top retention shelf 42 inside the cartridge nest 40, thereby enabling the medicine cartridge 20 to fit more snugly in the cartridge nest 40. If a plunger seal 88 on the plunger actuator 80 were to fail, the top face seal 30 may serve as a backup to prevent medication, fluid, or other liquids from leaking into the rest of the cartridge nest 40 and out of the cartridge nest cover 56.

As discussed above, the medicine cartridge 20 may contain a uniquely-keyed pattern 24 that may match the plunger actuator shaft 86 and the syringe body pattern 66. The unique pattern between the unique keyed pattern 24 of the medicine cartridge 20, the plunger actuator shaft 86, and the syringe body specially-shaped channel 66, may allow for a continuous channel that can alternate between a closed and open mode.

As set forth above, the device 10 includes a locking feature. This may allow for the device 10 to be locked absent proper authorization from an administrator or medical professional. This locking feature may prevent abuse of sensitive, harmful, or restricted medication from being administered absent the proper authorization. In one embodiment of the device 10, the medicine cartridge 20 may contain integrated passive electronics in the form of a barcode and radio frequency identification (RFID) chip 26. As such, the invention may comprise an RFID chip that may communicate with a compatible software, application, or other method of electronic communication, such that the device 10 may interchange between an active mode for injecting medicine and a locked mode which prevents the injection of medicine to the patient. One embodiment of the present invention utilizes the barcode and/or RFID chip 26 to store unique data information and digital security codes as part of the medicine cartridge 20. The medicine cartridge 20 may further comprise customizable information data and a digital security key stored in the medicine cartridge 20.

The device integrated electronics subassembly 120 can be adapted for communicating with the RFID chip 26 integrated in the medicine cartridge 20. The syringe integrated electronics subassembly 120 may have the ability to identify a designated medicine cartridge 20 and permit the syringe actuation mechanism, i.e. in the present device 10 the plunger actuator 80, only when desired by the operator and approved by a medical professional or proper administrator. The device 10 may be designed and implemented to prevent distribution or application of medication from the medicine cartridge 20 without the appropriate identification of patient and/or administrator, medicine, dose, schedule and the like. The medicine cartridge 20 may provide information, such as a unique code, barcode, identification number, or other method of identification as part of its unique identification. The integrated electronics subassembly 120 on the syringe body 60 may then read and verify the information of the medicine cartridge 20 information. Based on the information received, the device 10 may lock or unlock and prevent or allow the medicine to be delivered.

The medicine cartridge 20 may be located in the interior of the cartridge nest 40. The cartridge nest cover 56 may secure the medicine cartridge 20 inside the cartridge nest 40. In the preferred embodiment of the device 10, the medicine cartridge 20 may be removable from the device 10, such that multiple medicine cartridges 20 with different types of medicines may be compatible with the device 10, and such that the device 10 may be used multiple times with the same medicine cartridge 20 or it may be used with multiple medicine cartridges 20. The multiple medicine cartridges 20 may be contain the same medicines or they may contain different kinds of medicine or injectable fluid.

The plunger actuator 80 may act as the top pressure seal in the medicine cartridge 20 to inject medicine or fluid into a patient. When the plunger actuator shaft 86 feeds through the medicine cartridge pattern 24 it may push on the plunger seal 88 located in the interior of the device 10 and pressurize the liquid medicine within the medicine cartridge 20. In one embodiment of the device 10, there may be a bottom retention shelf 46 in the cartridge nest 40 that may be able to provide a pre-load against a bottom face seal 58 that may ensure the medicine cartridge 20 can fit securely in the cartridge nest 40.

As discussed above, the cartridge nest 40 may further comprise at least one cartridge nest tab 48 that may be used to secure the cartridge nest 40 into or to the syringe body 60, depending on the embodiment. The cartridge nest tab 48 may utilize a locking or securing mechanism well known in the art to connect, lock, and secure with the syringe body 60. The syringe body 60 may have an internal channel 64 that is adaptable to receiving the cartridge nest tab 48 that may snap into the syringe body internal channel 64 for retention.

In one embodiment of the device 10, the cartridge nest 40 may further comprise a contoured, flexible tip 50 for patient comfort. The cartridge nest 40 can also contain a channel cartridge nest channel 52 for an adjustable nose guard 100. As best illustrated in FIGS. 1-2, the cartridge nest 40 may comprise an integrated flexible application injector or tube 54 which may be made of soft rubber, plastic, or other applicable material intended to pass or snake through the patient's nasal cavities. It will be appreciated that the flexible application injector 54 can be of any suitable or desired length. The flexible application injector 54 may be of a length that is adapted for use with a particular patient. It is envisioned and appreciated that the effective length of the flexible application injector 54 may be reduced, extended, cut, trimmed, or otherwise adjusted to fit a particular patient or treatment method.

With reference still to FIGS. 1-2, the bottom face seal 58 may ensure that the medicine, while injected into the patient, does not leak around the cartridge into the cartridge nest body 44, and potentially through the cartridge nest cover 56. The disposable, perforated seal 90 may act to contain the medicine or fluid in the medicine cartridge 20 until the medicine or fluid is pressurized by the plunger seal 88 pushed by the plunger actuator 80. This plunger seal 88 may break and open under pressure to release the medicine. This plunger seal 88 may be the final design or representative of any method designed to allow the flow of medicine while the plunger actuator 80 is actuated.

In one embodiment of the present invention, the device 10 may be collapsible, disassembled, or otherwise shortened in order to reduce its overall length for storage and transportation. For example, the contoured applicator tip 50 can become a telescopic device and be stored within the tip of the cartridge nest 40. The plunger actuator 80 can also become a telescopic device, and the length of the plunger actuator 80 beyond the retention surface can collapse into the length that is within the syringe body 60.

The device 10 may be configured so that the integrated electronics and lock subassembly 120 may communicate with a dedicated application installed on a smartphone, tablet, or other mobile device (not shown). However, it will be appreciated that the application and/or its user interface may also be installed or displayed on any suitable device, including but not limited to, a laptop computer, desktop computer, wearable device, smart appliance, infotainment system, gaming system, television, media player, e-reader, or any other electronic device suitable for running software applications. The device integrated electronics and lock subassembly 120 may have the ability to be paired with and communicate via Bluetooth connectivity, Wi-Fi connectivity, or other wireless or hardwired communication standard with a device, such as a smartphone or tablet device.

The dedicated software application developed for the smartphone, tablet, or other devices device can have the ability to interact with the patient and/or the administrator. The software application provides a convenient user interface allowing pre-programing of the syringe applicator. Thus, the patient information, medication, dosage schedule and other parameters can be pre-programed and downloaded to the syringe applicator electronics. As a result, the syringe applicator can be used independently by the patient and/or administrator. In addition, the software application can utilize built in camera and/or microphone components of a smartphone, tablet, or other device as a photographic and/or speech recognition security feature. The authorized patient or administrator can be permitted to set a unique customizable user profile in the software application with the ability to store the user's facial pictures, speech recordings, fingerprint data, retina data, vein or other eye data, or other suitable biometric information of the user. These pictures and/or voice recordings may be utilized to perform a secure user authentication by which to permit usage of the software application and syringe apparatus. As a result, in one embodiment, the software application will only permit activation of the syringe applicator when the (1) designated user is identified; (2) the correct medication cartridge is inserted in the syringe; (3) the pre-programmed dosage is prescribed; and (4) the pre-programmed scheduled dosage time period is active. The software application can also securely transmit the syringe applicator medication and patient usage information to the medical provider's electronic medical records. As a result, the patient's medical record can be updated in real-time with the medication usage information. Examples of the integrated electronics and software application are illustrated in FIGS. 6-7.

For each medicine cartridge 20 with integrated electronics and lock subassembly 120, the manufacturer may populate the electronic section of the medicine cartridge 20 with a unique serial and hash data identifiers which enable the medicine cartridge 20 to be registered as a digital asset on a Blockchain network. Once the product is registered to the Blockchain by the manufacturer, its ownership can be readily transferred and tracked in the distribution supply chain.

When fully assembled, the device 10 may be used to inject medicine into a patient securely, safely, and in a manner that prevents abuse. In one embodiment as illustrated in FIGS. 1-2, the device 10 may be in a secured and locked state. In this state, the electronics and lock subassembly 120 may function as an interference locking device and may have the high strength levers 122 extended into the syringe body 60, locking in place in the syringe body channel 64. The levers 122 in this position may create an interference in the syringe and may prevent the plunger actuator 80 from pushing through the syringe body 60, the medicine cartridge 20, thereby preventing the medicine from being pushed through the cartridge nest channel 52 and integrated flexible application injector 54. When the patient receives authorization from a medical professional or administrator, or when a medical professional or administrator unlocks the device 10 using the electronics of the medicine cartridge 20, the patient, medical professional, or administrator may use the direction and selection buttons located on the electronics and lock subassembly body 128 to unlock the device 10 and retract the levers 122 from the syringe body channel 64. When the levers 122 are removed from the syringe body channel 64, the plunger actuator 80 may then be pushed through the device 10 to administer medicine. The security system of the device 10 may allow for the specially shaped elongated plunger shaft 86 to pass through the specially-shaped channel 66 of the syringe body 60, and the specially-shaped medicine cartridge pattern 24 of the medicine cartridge 20.

The device 10 may be used to administer medicine to a patient by inserting the integrated flexible application injector 54 into the nose of the patient. The integrated flexible application injector 54 may be of an appropriate length depending on the patient to enter the nasal cavity of the patient. The device 10 may continue into the nasal cavity of the patient until the contoured tip 50 reached the nostril of the patient. Because of its contoured design, the contoured tip 50 may enter safely and comfortably into the nostril of the patient. To prevent the device 10 from entering too far into the patient, the nose ring 100 may prevent the device from entering any further into the patient. When the device 10 is in the appropriate position in the nasal cavity, the plunger actuator 80 may then be used to administer medicine. The patient, medical professional, or administrator may use the plunger actuator finger engagement surface 82 and the syringe body handle 62 to press the plunger actuator 80 through the device. The plunger seal 88 may be used to push the medicine from the medicine cartridge 20 through the cartridge nest channel 52. When pushed through the cartridge nest channel 52, the pressurized medicine or fluid may break the disposable, perforated seal 90, which may act to prevent leaking of fluid before the plunger actuator 80 pushes the medicine through the device 10. The medicine may continue to be pushed through the cartridge nest channel 52 through the integrated flexible application injector 54 and into the nasal cavity of the patient. When the medicine is administered, the device 10 may be removed from the patient. In one embodiment of device 10, the medicine cartridge 20 is a single-use cartridge capable of delivering one dosage of medicine. In one embodiment, the medicine cartridge 20 may be removed from the device 10 by removing the syringe body 60 and the cartridge nest cover 56. In this embodiment, a new medicine cartridge 20 may be placed in the cartridge nest 40 for administering medicine.

FIGS. 8-13 provide flowcharts of methods for administering, scheduling, notifying, setting up user profiles, auditing, and authenticating. These flowcharts demonstrate the security electronics logic and outline the processes the software and electronics will follow in different circumstances.

Figure 8:
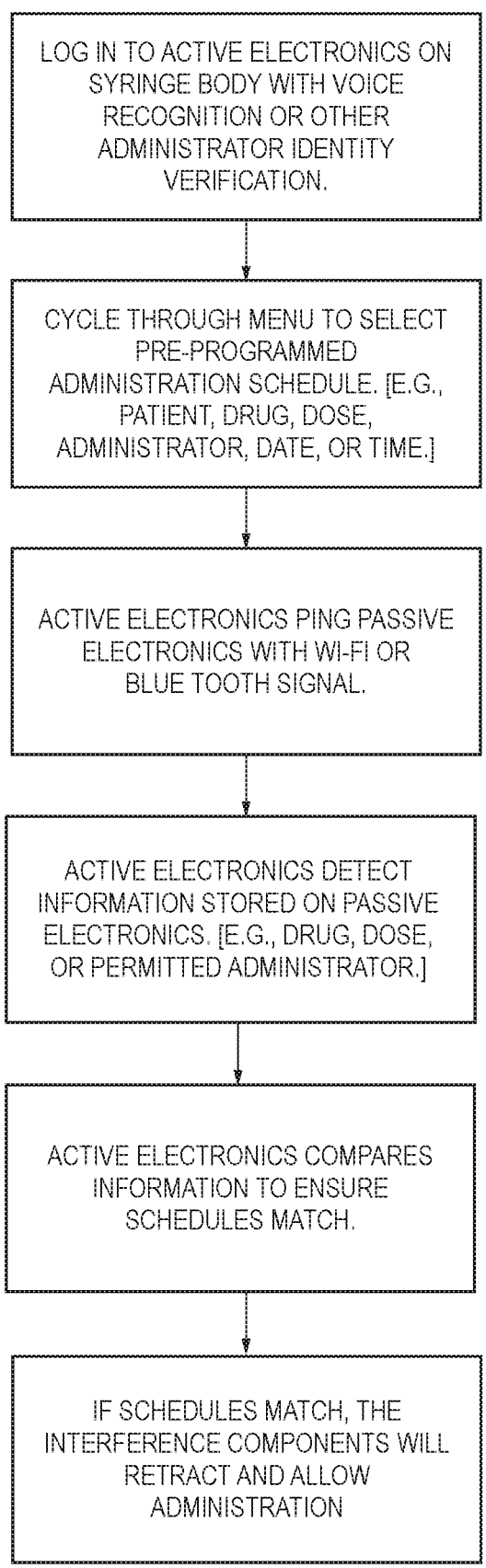
FIG. 8 is a flowchart illustrating operations of a method for administering medication through a secure syringe in accordance with one embodiment of the present invention.

One such method is illustrated in FIG. 8. In this method of use, an administrator or medical professional may log in to the operating system or software compatible with the device 10 to activate the integrated electronics on the syringe body 60 with voice recognition or other administrator identity verification. The administrator or authorized user may then cycle through the menu to select pre-programmed administration schedule, with information include without limitation patient information, drug information, dose information, administrator information, date, and time. The active electronics of the device 10 may ping passive electronics with Wi-Fi, Bluetooth, or other methods of signal communication. The active electronics of the device 10 may detect information stored on the passive electronics, including without limitation, patient information, drug information, dose information, administrator information, date, and time. The active electronics can then compare information to ensure that schedules of the active electronics match the pre-programmed administration schedule. If the schedules match, the interference components (i.e., the levers 122) may retract and allow administration of medicine to the patient.

Figure 9:
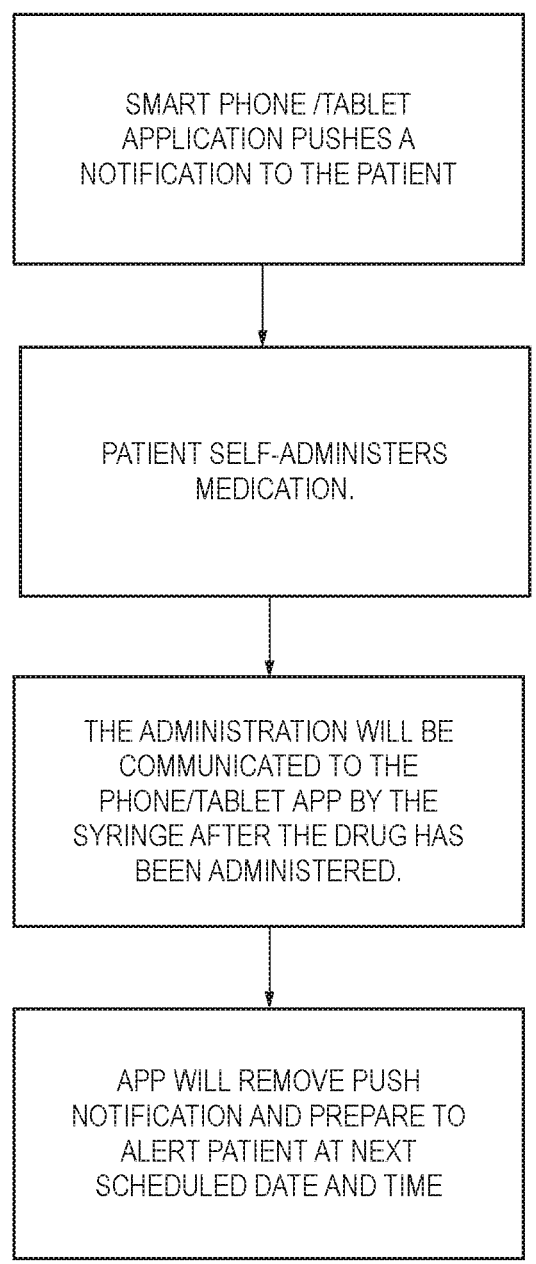
FIG. 9 is a flowchart illustrating operations of a method for notifying a user to administer a medicinal treatment in accordance with one embodiment of the present invention.

Another such method is illustrated in FIG. 9. In this method of use, a smart phone, computer, tablet or other device application may push a notification to the patient. The patient may then self-administer the medication using the device 10. The administration, medical professional, or other authorization authority may be communicated to the phone, tablet, or other device app by the device 10 after the drug has been administered. After administration, the application may remove the push notification and can then prepare to alert the patient at the next scheduled date and time.

Figure 10:
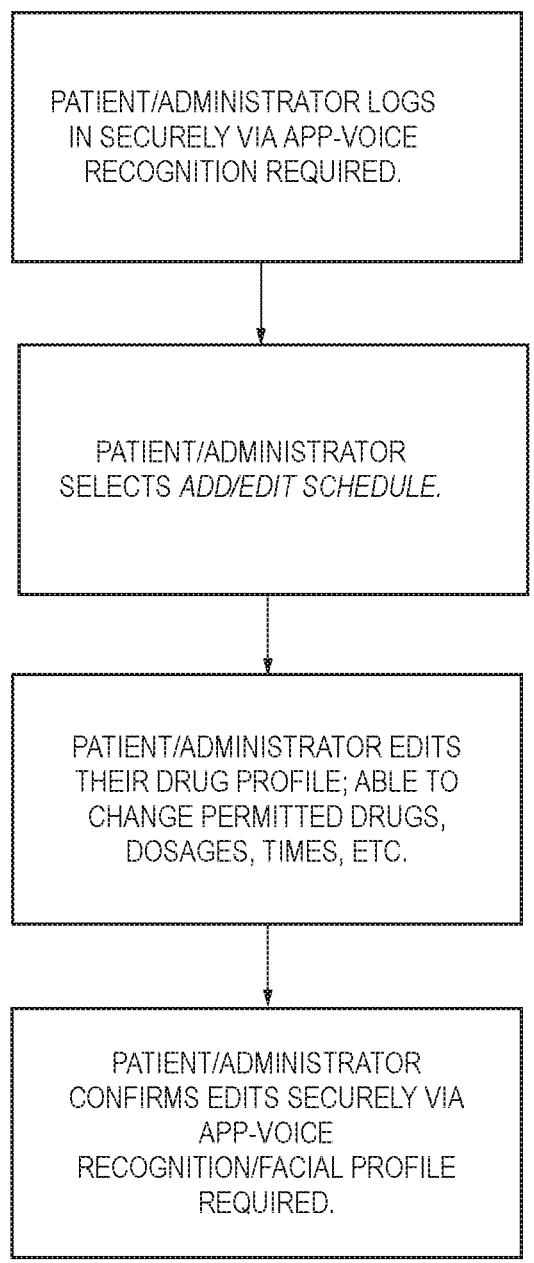
FIG. 10 is a flowchart illustrating operations of a method for setting and modifying scheduling and dosages of medicinal treatments administered through a secure syringe in accordance with one embodiment of the present invention.

Another such method is illustrated in FIG. 10. In this method of use, the patient or administrator may log in securely to the program using a phone, tablet, or other device application. In this particular method, the application may use voice recognition as a method of security. The patient or administrator may then select a pre-programmed option including without limitation an Add Schedule or Edit Schedule option. The patient or administrator may then edit the drug profile, may change the permitted drugs, the dosages, the times and other options. The patient or administrator may then confirm their option selection or edits by using the application, and for added security this method may use voice recognition or facial recognition.

Figure 11:
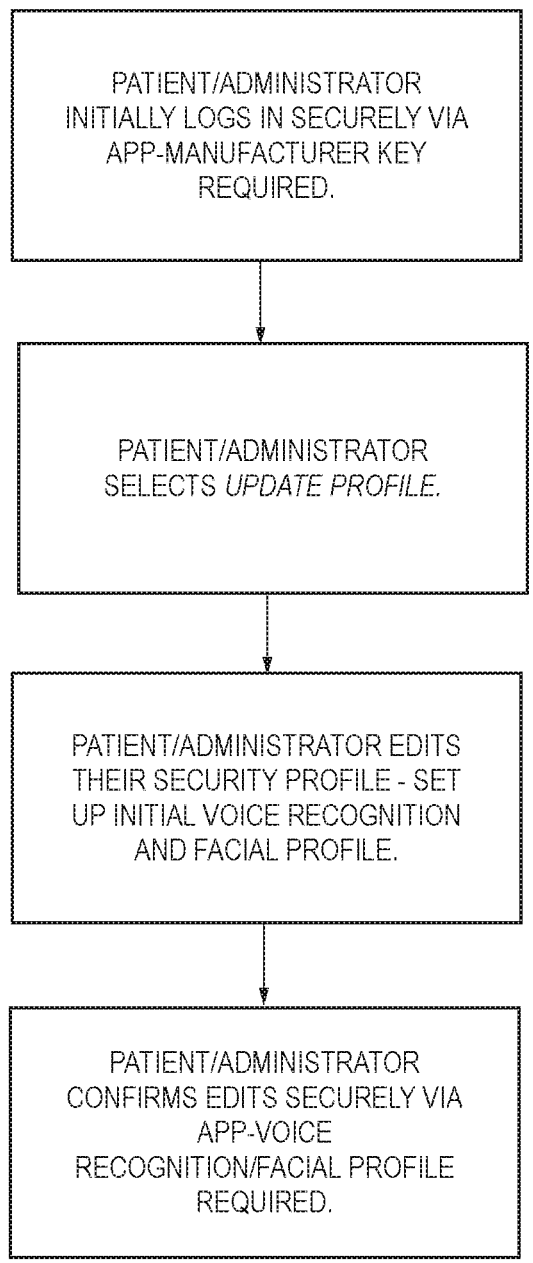
FIG. 11 is a flowchart illustrating operations of a method for adding and editing user security profile data in accordance with one embodiment of the present invention.

Another such method of use is illustrated in FIG. 11. In this method of use, the patient or administrator may initially log in to the mobile, phone, tablet, or other device application using a manufacturer key. The patient or administrator may then select the Update Profile option on the application. The patient or administrator may then edit their security profile and may further set up initial voice recognition and facial profile. The patient or administrator may then confirm the edits securely via the application, and in this particular method, the patient or administrator may use voice recognition or facial recognition to confirm.

Figure 12:
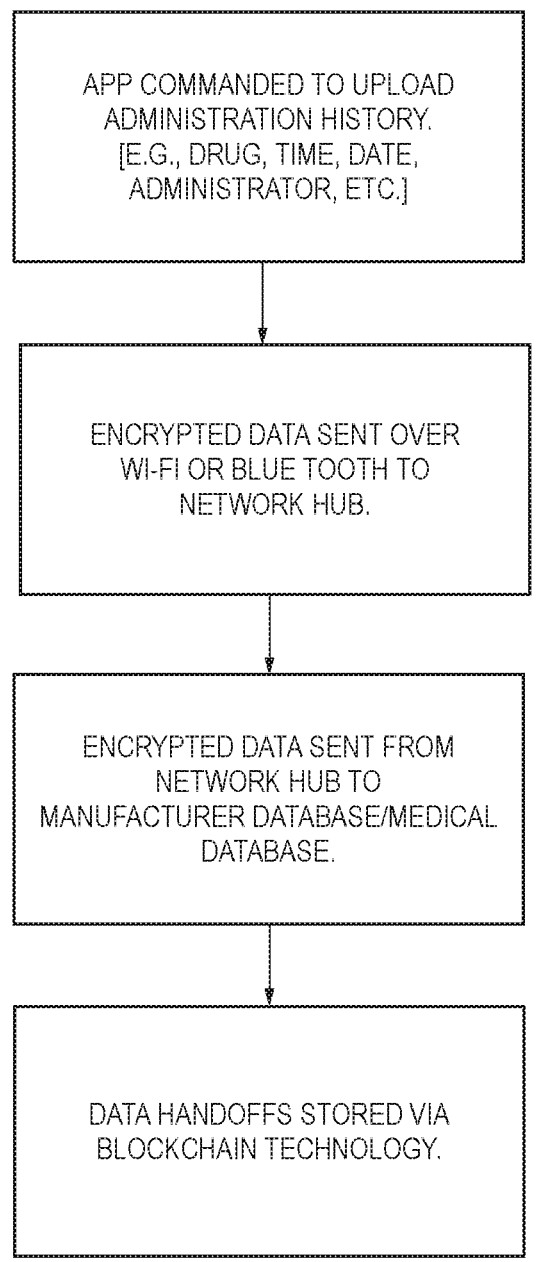
FIG. 12 is a flowchart illustrating operations of a method for auditing the administration of medicinal treatments in accordance with one embodiment of the present invention.

Another such method of use is illustrated in FIG. 12. In this method the patient or administrator may use the application to command an upload of administration history, such information in the history may include, without limitation, patient information, drug information, dose information, administrator information, date, and time. The information uploaded may be encrypted and the data may be sent over Wi-Fi or Bluetooth to a network hub that may securely store the information. The encrypted data may be sent from the network hub to a manufacturer database or medical database. The handoff of data may be stored via Blockchain technology.

Figure 13:
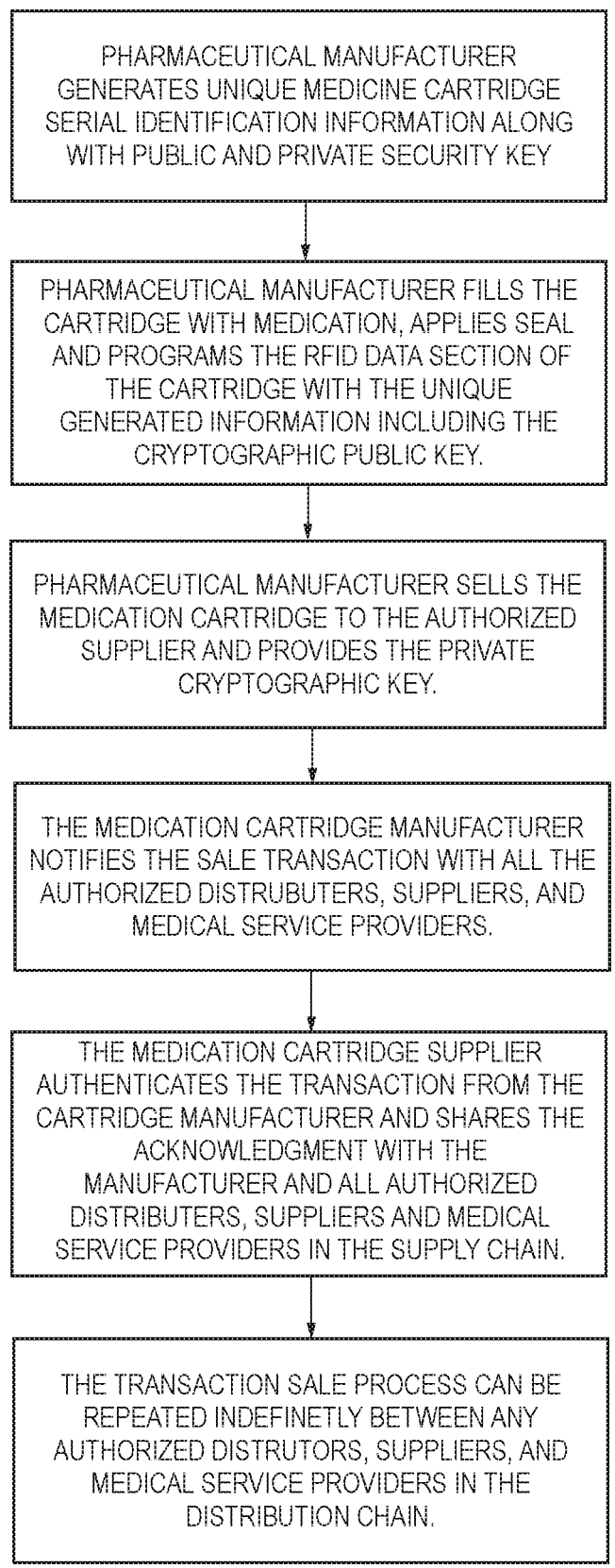
FIG. 13 is a flowchart illustrating operations of a method for manufacturer and supply chain authentication in accordance with one embodiment of the present invention.

Another such method of use is illustrated in FIG. 13. In this method the pharmaceutical manufacturer may generate the unique medicine cartridge serial identification information along with a public and private security key. The pharmaceutical manufacturer may then fill the medicine cartridge 20 with medication, and apply a seal to the medicine cartridge, and may further program the RFID data section of the medicine cartridge with the unique generated information including the cryptographic public key. The pharmaceutical manufacturer may then sell the medicine cartridge to an authorized supplier and may provide the private cryptographic key. The medicine cartridge manufacturer may then notify the sale transaction with all the authorized distributor, supplier, and medical service providers. The medication cartridge supplier may then authenticate the transaction from the cartridge manufacturer and share the acknowledgment with the manufacturer and all authorized distributors, suppliers, and medical service providers in the supply chain. The transaction sale process can be repeated indefinitely between any authorized distributors, suppliers and/or medical service providers in the distribution chain.

Figure 14:
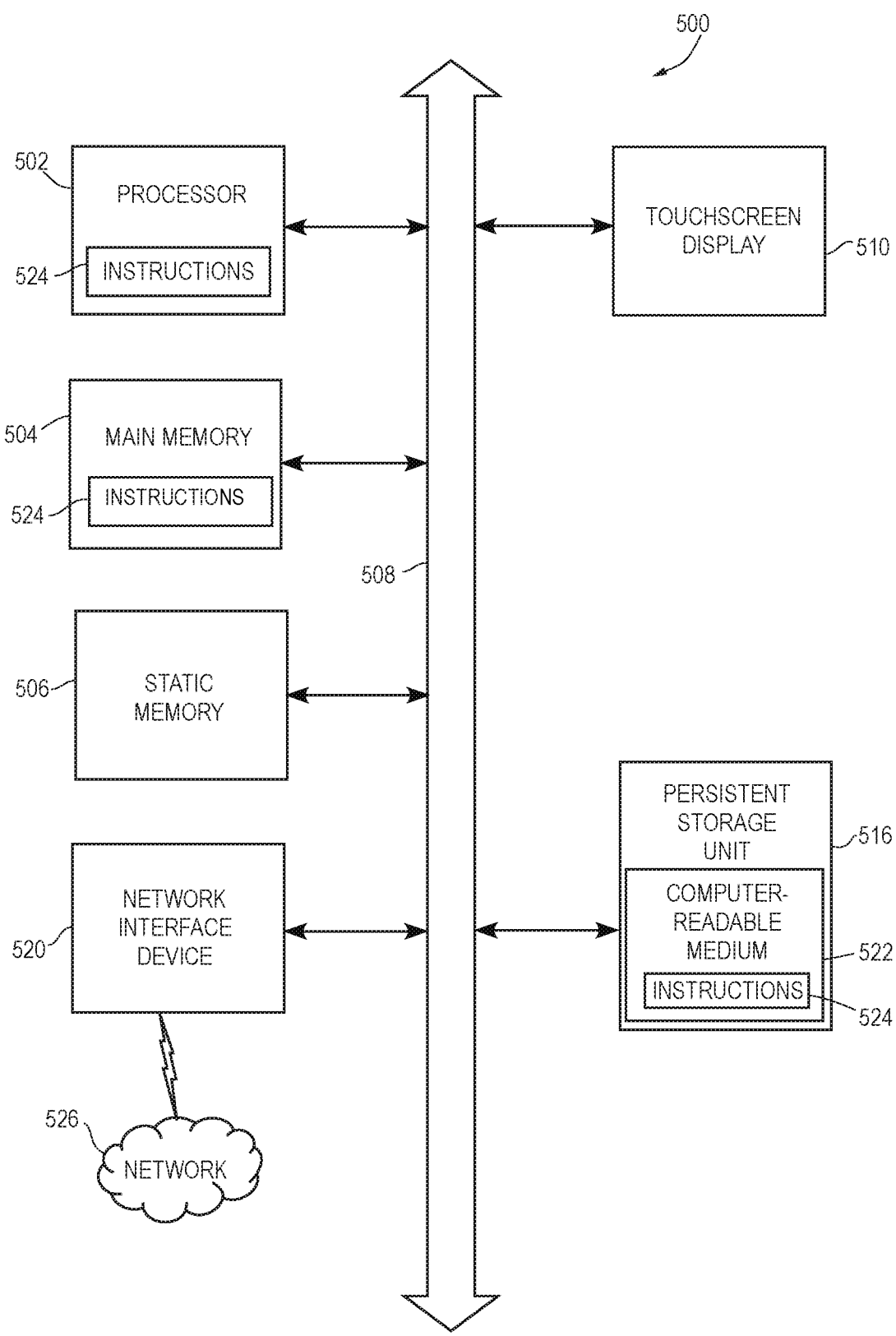
FIG. 14 is a block diagram of an example embodiment of a computer system upon which embodiments of the inventive subject matter can execute in accordance with one embodiment of the present invention.

With reference to FIG. 14, an example embodiment of a method of using the present invention extends to a machine in the example form of a computer system 500 within which instructions for causing the machine to perform any one or more of the methodologies discussed herein may be executed. In alternative example embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. Further, while only a single machine is illustrated, the term "machine" shall also be taken to include any collection of machines that individually or jointly execute a set (or multiple sets) of instructions to perform any one or more of the methodologies discussed herein.

The example computer system 500 may include a processor 502 (e.g., a central processing unit (CPU), a graphics processing unit (GPU) or both), a main memory 504 and a static memory 506, which communicate with each other via a bus 508. The computer system 500 may further include a touchscreen display unit 510. In example embodiments, the computer system 500 also includes a network interface device 520.

The persistent storage unit 516 includes a machine-readable medium 522 on which is stored one or more sets of instructions 524 and data structures (e.g., software instructions) embodying or used by any one or more of the methodologies or functions described herein. The instructions 524 may also reside, completely or at least partially, within the main memory 504 or within the processor 502 during execution thereof by the computer system 500, the main memory 504 and the processor 502 also constituting machine-readable media.

While the machine-readable medium 522 is shown in an example embodiment to be a single medium, the term "machine-readable medium" may include a single medium or multiple media (e.g., a centralized or distributed database, or associated caches and servers) that store the one or more instructions. The term "machine-readable medium" shall also be taken to include any tangible medium that is capable of storing, encoding, or carrying instructions for execution by the machine and that cause the machine to perform any one or more of the methodologies of embodiments of the present invention, or that is capable of storing, encoding, or carrying data structures used by or associated with such instructions. The term "machine-readable storage medium" shall accordingly be taken to include, but not be limited to, solid-state memories and optical and magnetic media that can store information in a non-transitory manner, i.e., media that is able to store information. Specific examples of machine-readable storage media include non-volatile memory, including by way of example semiconductor memory devices (e.g., Erasable Programmable Read-Only Memory (EPROM), Electrically Erasable Programmable Read-Only Memory (EEPROM), and flash memory devices); magnetic disks such as internal hard disks and removable disks; magneto-optical disks; and CD-ROM and DVD-ROM disks. A machine-readable storage medium does not include signals.

The instructions 524 may further be transmitted or received over a communications network 526 using a signal transmission medium via the network interface device 520 and utilizing any one of a number of well-known transfer protocols (e.g., FTP, HTTP). Examples of communication networks include a local area network (LAN), a wide area network (WAN), the Internet, mobile telephone networks, Plain Old Telephone (POTS) networks, and wireless data networks (e.g., WiFi and WiMax networks). The term "machine-readable signal medium" shall be taken to include any transitory intangible medium that is capable of storing, encoding, or carrying instructions for execution by the machine, and includes digital or analog communications signals or other intangible medium to facilitate communication of such software.

From the foregoing, it will be seen that this invention is one well adapted to attain all the ends and objects hereinabove set forth together with other advantages which are inherent to the structure and method. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A secure device for delivering a medication, the device comprising:
    a syringe body;
    a plunger actuator; and
    an electronic lock subassembly including a first extendable and retractable locking portion and a second extendable and retractable locking portion, wherein the first extendable and retractable locking portion is disposed adjacent to a first side of the plunger actuator and the second extendable and retractable locking portion is disposed adjacent to a second side of the plunger actuator, wherein the first extendable and retractable locking portion and the second extendable and retractable locking portion extend and retract in the same direction relative to one another, and wherein when extended, the first extendable and retractable locking portion and the second extendable and retractable locking portion prevent a finger engagement surface of the plunger actuator from moving axially relative to the syringe body thereby preventing administration of the medication until specific conditions are met.

2. The device of claim 1, wherein the device is suitable for delivering intranasal medications and further comprises a flexible application injector and a nose guard.

3. The device of claim 1 further comprising a cartridge nest and a medicine cartridge with integrated electronics, wherein the cartridge nest is adapted for receiving the medicine cartridge.

4. The device of claim 3, wherein the medicine cartridge may further comprise at least one of an RFID chip, customizable information data, and a digital security key stored therein.

5. The device of claim 3, wherein the medicine cartridge may further comprise a specific pre-loaded amount of medication.

6. The device of claim 5, wherein the medicine cartridge may be used for a single administration of medication.

7. The device of claim 3, wherein the medicine cartridge is programmed with a unique serial and hash data identifier to enable the medicine cartridge to be registered as a digital asset on a Blockchain network.

8. The device of claim 3, wherein the syringe body and medicine cartridge each include a channel defined therethrough, wherein the channels have matching patterns.

9. The device of claim 8, wherein the plunger actuator includes a cross-section having a pattern that matches the patterns of the syringe body channel and the medicine cartridge channel.

10. The device of claim 3, wherein the medicine cartridge is pre-programmed with patient and usage information.

11. The device of claim 1, wherein the device selectively notifies a patient and/or administrator when a dosage is required.

12. The device of claim 1, wherein the electronic lock subassembly is adapted to only permit administration of medication when an appropriate medication dosage is loaded in the device.

13. The device of claim 1, wherein the device is adapted to only permit administration of medication when an appropriate scheduled dosage time period is active.

14. The device of claim 1, wherein the electronic lock subassembly further comprises an interface with a user and/or administrator provided smartphone, tablet, or computer device.

15. The device of claim 1, wherein the electronic lock subassembly is adapted to be pre-programmed by a user and/or administrator via a smartphone, tablet, or computer application.

16. The device of claim 1, wherein the electronic lock subassembly further comprises a uniquely customizable user profile for storing at least one of a user's facial picture and voice recording.

17. The device of claim 16, wherein the electronic lock subassembly only permits administration of medication when a patient and/or administrator is verified via at least one of facial and voice recognition.

18. The device of claim 1, wherein the first extendable and retractable locking portion and the second extendable and retractable locking portion are parallel with one another.

19. The device of claim 18 further comprising:
    the syringe body including a passage defined therethrough, the passage having a cross-sectional shape having a pattern; wherein a pattern of a cross-sectional shape of the plunger actuator matches the pattern of the cross-sectional shape of the syringe body passage.

* * * * *